(12) United States Patent
Suzuki et al.

(10) Patent No.: US 10,194,984 B2
(45) Date of Patent: Feb. 5, 2019

(54) OPTICAL COSMETIC DEVICE FOR BODILY HAIR

(71) Applicant: Panasonic Intellectual Property Management Co., Ltd., Osaka (JP)

(72) Inventors: Kaori Suzuki, Osaka (JP); Masato Kinoshita, Shiga-ken (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 278 days.

(21) Appl. No.: 14/421,583

(22) PCT Filed: Jan. 10, 2014

(86) PCT No.: PCT/JP2014/000092
§ 371 (c)(1),
(2) Date: Feb. 13, 2015

(87) PCT Pub. No.: WO2014/129100
PCT Pub. Date: Aug. 28, 2014

(65) Prior Publication Data
US 2015/0230862 A1 Aug. 20, 2015

(30) Foreign Application Priority Data
Feb. 22, 2013 (JP) ............... 2013-0338900

(51) Int. Cl.
*A61B 18/18* (2006.01)
*A61B 18/00* (2006.01)
(52) U.S. Cl.
CPC .... *A61B 18/18* (2013.01); *A61B 2018/00476* (2013.01); *A61B 2018/1807* (2013.01)

(58) Field of Classification Search
CPC .......... A61B 18/18; A61B 2018/00476; A61B 2018/1807
See application file for complete search history.

(56) References Cited

U.S. PATENT DOCUMENTS

| 6,235,016 B1 | 5/2001 | Stewart |
| 2002/0022828 A1 | 2/2002 | Stewart |

(Continued)

FOREIGN PATENT DOCUMENTS

| JP | 99/32193 A1 | 7/1999 |
| JP | 2007-502141 A | 2/2007 |

(Continued)

OTHER PUBLICATIONS

Extended European Search Report issued in European Application No. 14754740.0 dated Feb. 18, 2016.

(Continued)

*Primary Examiner* — Daniel L Cerioni
*Assistant Examiner* — Yasmeen S Warsi
(74) *Attorney, Agent, or Firm* — McDermott Will & Emery LLP

(57) ABSTRACT

This optical cosmetic device for bodily hair is provided with optical systems for illumination with cosmetic light for bodily hair. The value of the integral of the intensity of the cosmetic light for bodily hair in the 800 nm-1200 nm wavelength range is greater than that in the 400 nm-800 nm wavelength range. The value of the integral of the intensity of the cosmetic light for bodily hair in the 400 nm-850 nm wavelength range is less than that in the 850 nm-1200 nm wavelength range.

6 Claims, 5 Drawing Sheets

(56) References Cited

U.S. PATENT DOCUMENTS

| | | | |
|---|---|---|---|
| 2002/0173780 A1 | 11/2002 | Kltshuler et al. | |
| 2004/0010298 A1 | 1/2004 | Kltshuler et al. | |
| 2005/0107850 A1 | 5/2005 | Vaynberg et al. | |
| 2006/0241726 A1* | 10/2006 | Whitehurst .......... | A61N 5/0616 607/86 |
| 2006/0247740 A1 | 11/2006 | Roersma et al. | |
| 2007/0203447 A1 | 8/2007 | Jun | |

FOREIGN PATENT DOCUMENTS

| | | |
|---|---|---|
| JP | 2007-502642 A | 2/2007 |
| JP | 2007-229459 A | 9/2007 |
| WO | 81/00677 A1 | 3/1981 |

OTHER PUBLICATIONS

International Search Report issued in PCT/JP2014/000092, dated Mar. 18, 2014, with English translation.
English Translation of International Preliminary Report on Patentability issued in Application No. PCT/JP20141000092 dated Aug. 25, 2015.
European Search Report dated Feb. 23, 2017 issued in European Patent Application No. 14754740.0.

\* cited by examiner

OPTICAL COSMETIC DEVICE FOR BODILY HAIR

RELATED APPLICATIONS

This application is the U.S. National Phase under 35 U.S.C. § 371 of International Application No. PCT/JP2014/000092, filed on Jan. 10, 2014, which in turn claims the benefit of Japanese Application No. 2013-033890, filed on Feb. 22, 2013, the disclosures of which Applications are incorporated by reference herein.

TECHNICAL FIELD

The present invention relates to an optical cosmetic device for body hair.

BACKGROUND ART

Patent document 1 discloses a conventional optical cosmetic device for body hair. The optical cosmetic device for body hair of patent document 1 is configured to irradiate skin with light having a wavelength range of 550 nm to 1200 nm in order to inhibit hair growth.

Patent Document 1: Japanese National Phase Laid-Open Patent Publication No. 2007-502642

SUMMARY OF THE INVENTION

The inventors of the present application noticed that light emitted by the cosmetic device for body hair of patent document 1 has a broad wavelength range and includes many components that does not contribute or only slightly contribute to inhibiting hair growth. Thus, energy is not effectively used for inhibiting the growth of body hair.

It is an object of the present invention to provide an optical cosmetic device for body hair that can effectively inhibit the growth of body hair.

One aspect of the present invention is an optical cosmetic device for body hair including an optical system that emits cosmetic light for body hair. An intensity integral of the cosmetic light for body hair is larger in a wavelength range of 800 nm to 1200 nm than in a wavelength range of 400 nm to 800 nm, and an intensity integral of the cosmetic light for body hair is smaller in a wavelength range of 400 nm to 850 nm than in a wavelength range of 850 nm to 1200 nm.

In one example, the intensity integral of the cosmetic light for body hair is smaller in the wavelength range of 400 nm to 850 nm than in the wavelength range of 900 nm to 1200 nm.

In one example, the intensity integral of the cosmetic light for body hair is smaller in the wavelength range of 400 nm to 850 nm than in the wavelength range of 950 nm to 1200 nm.

In one example, the intensity integral of the cosmetic light for body hair is larger in the wavelength range of 800 nm to 1000 nm than in the wavelength range of 1000 nm to 1200 nm.

In one example, the intensity integral of the cosmetic light for body hair is larger in the wavelength range of 850 nm to 1000 nm than in the wavelength range of 1000 nm to 1200 nm.

In one example, the intensity integral of the cosmetic light for body hair is larger in the wavelength range of 900 nm to 1000 nm than in the wavelength range of 1000 nm to 1200 nm.

In one example, the cosmetic light for body hair has no intensity peaks in a wavelength range of 800 nm to 860 nm.

In one example, the optical system comprises a xenon lamp and a band-pass filter, the xenon lamp emits light in a wavelength range of 400 nm to 1200 nm, and the band-pass filter forms the cosmetic light for body hair by cutting light of wavelengths other than the wavelength range of 800 nm to 1200 nm.

The inventors of the present application studied the relationship between light in a wavelength range of 400 nm to 1200 nm and the body hair cosmetic treatment effect. The inventors have identified cosmetic light for the optical cosmetic device for body hair based on the findings of the study. The term body hair cosmetic treatment effect used in the present specification indicates the inhibition effect or depilation effect on the living body. The term inhibition of hair used in the present specification indicates the effect for inhibiting body hair reproduction and growth on a living body. Depilation indicates an effect for removing body hair from a living body.

The inventors of the present application defined a plurality of wavelength ranges in the wavelength range of 400 nm to 1200 nm, and have conducted experiments to check the relationship between optical energy in each of the wavelength ranges and the body hair cosmetic treatment effect. The results of the experiments showed that light in the wavelength range of 400 nm to 850 nm enhances the body hair cosmetic treatment effect with respect to the amount of optical energy at a lower degree than light in the wavelength range of 850 nm to 1200 nm. The results of the experiments do not show that the light of each wavelength in the wavelength range of 400 nm to 850 nm enhances the body hair cosmetic treatment effect at a lower degree than the light of each wavelength in the wavelength range of 850 nm to 1200 nm. More specifically, the results of the experiments show that when comprehensively comparing the light in the above two wavelength ranges, the light in the wavelength range of 850 nm to 1200 nm can more effectively enhance the body hair cosmetic treatment effect than the light in the wavelength range of 400 nm to 850 nm.

The inventors of the present application, from the above experiment results, found the cosmetic light for body hair that effectively enhances the body hair cosmetic treatment effect. The inventors of the present application defined, in the cosmetic light for body hair, a light source spectrum in which an intensity integral is smaller in a wavelength range of 400 nm to 850 nm than in a wavelength range of 850 nm to 1200 nm. Therefore, the cosmetic light for body hair is smaller in the amount of optical energy in the wavelength range of 400 nm to 850 nm than in the wavelength range of 850 nm to 1200 nm.

Each of the above-described optical cosmetic devices for body hair emits cosmetic light for body hair. Therefore, as compared to when the intensity integral is larger in the wavelength range of 400 nm to 850 nm than in the wavelength range of 850 nm to 1200 nm, the body hair cosmetic treatment effect can be enhanced effectively more easily. Therefore, the optical cosmetic device for body hair can effectively inhibit the growth of body hair.

Effects of the Invention

The optical cosmetic device for body hair can effectively inhibit the growth of body hair.

DESCRIPTION OF EMBODIMENTS

First Embodiment

Figure 1:
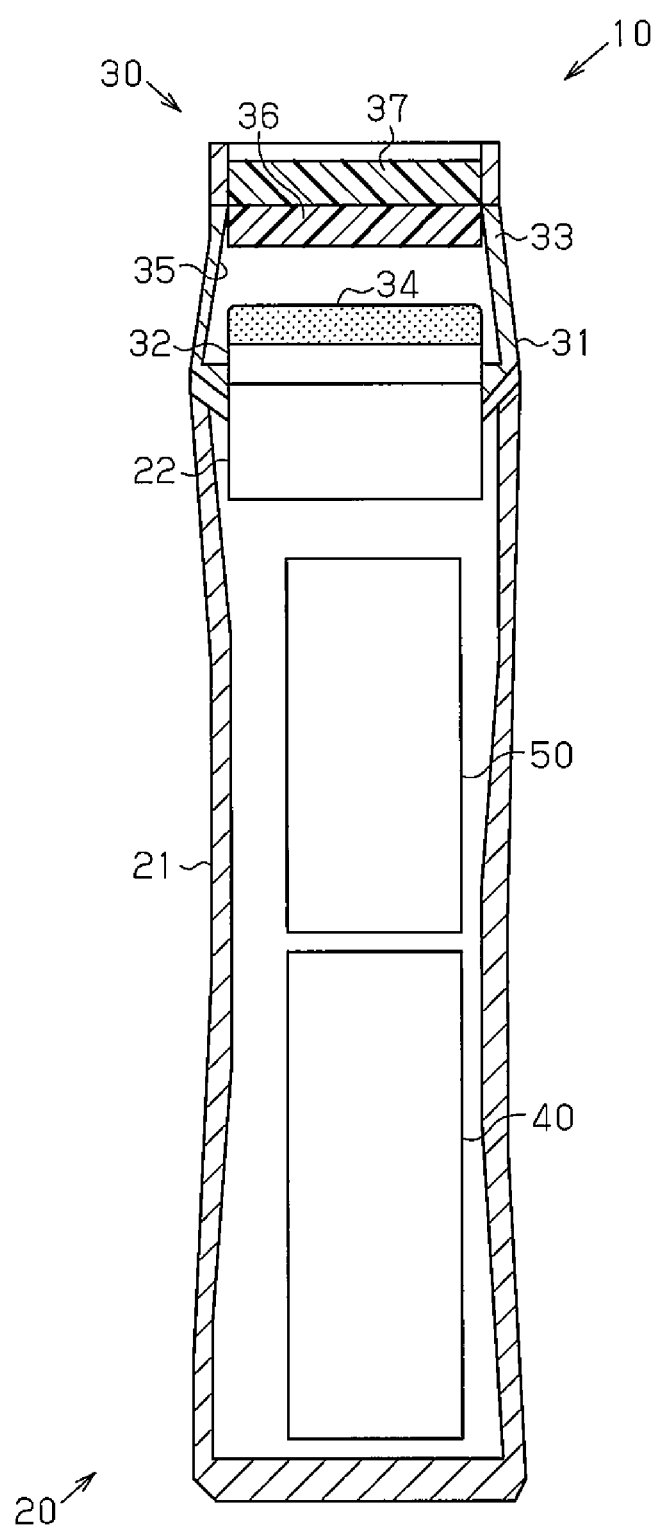
FIG. 1 is a schematic diagram showing a configuration of an optical cosmetic device for body hair of a first embodiment.

A body hair optical cosmetic device 10 is configured as shown in FIG. 1 for example. The body hair optical cosmetic device 10 effectively enhances the body hair cosmetic treatment effect on a living body by irradiating the living body with cosmetic light for body hair. The body hair optical cosmetic device 10 irradiates a living body with cosmetic light for body hair to obtain a cosmetic treatment enhancement effect and a side effect inhibition effect. The term cosmetic treatment enhancement effect used in the present specification indicates an effect of inhibiting the growth of body hair by enhancing the body hair cosmetic treatment effect. The term side effect inhibition effect indicates an effect limiting unwanted side effects on the skin. The body hair optical cosmetic device 10 has a main body 20, a light source unit 30, a power supply circuit unit 40, and a control unit 50.

The main body 20 is shaped so that it can be held by a user, for example. The main body 20 includes, for example, a body housing 21 and a body connector 22. The main body 20 includes multiple components that are integrated together.

The body housing 21 is formed from resin material for example. The body housing 21 is vertically long. The body housing 21 has an internal space. The body housing 21 accommodates the power supply circuit unit 40 and the control unit 50 in its internal space.

The body connector 22 is connected to the body housing 21. The body connector 22 is electrically connected to the power supply circuit unit 40. The body connector 22 is mechanically connectable to and separable from a light source connector 32. When mechanically connected to the light source connector 32, the body connector 22 is electrically connected to the light source connector 32.

The light source unit 30 may be, for example, an attachment that can be attached to or detached from the main body 20. The light source unit 30 includes, for example, a light source housing 31, the light source connector 32, a filter mounting part 33, a light source 34, a reflector 35, a lens 36, and an optical filter 37. The light source unit 30 includes multiple components integrated together. The light source unit 30 includes the optical filter 37 that is replaceable with another optical filter. The light source unit 30 can change the spectrum of light emitted from the light source 34 in accordance with the type of optical filter 37.

The light source housing 31 may be formed from a resin material. The light source housing 31 has a shape similar to a cylinder. The light source housing 31 has an internal space. The light source housing 31 accommodates the light source 34, the reflector 35, and the lens 36 in its internal space. The light source housing 31 includes a foreign matter penetration preventing structure to prevent external dust or other foreign matter from entering the internal space of the light source housing 31. The light source housing 31 absorbs light with a specific wavelength range. The light source housing 31 absorbs light in a wavelength range of less than 800 nm for example. The light source housing 31 absorbs light in a wavelength range of 400 nm or greater to less than 800 nm for example.

The light source connector 32 is connected to the light source housing 31. The light source connector 32 is electrically connected to the light source 34. The light source connector 32 is mechanically connectable to and separable from the body connector 22. When mechanically connected to the body connector 22, the light source connector 32 is electrically connected to the body connector 22.

The filter mounting part 33 has a shape similar to an annular ring. The filter mounting part 33 is arranged at an opening of the light source housing 31. The filter mounting part 33 is connected to the light source housing 31. The filter mounting part 33 is mechanically connectable to and separable from the optical filter 37.

The light source 34 is arranged in the internal space of the light source housing 31. The light source 34 is connected to the light source housing 31. The light source 34 is electrically connected to the light source connector 32. The light source 34 includes, for example, a xenon flash lamp, a laser, a light-emitting diode (LED), or an organic electroluminescence (EL). In one example, the light source 34, which is a xenon flash lamp, applies light containing components having wavelengths of 400 to 1200 nm.

The reflector 35 is formed from a highly reflective material. The reflector 35 is formed from, for example, a metal material, a resin material, or ceramic. The reflector 35 preferably has a surface processed to increase the reflectivity of light emitted from the light source 34. The processed surface includes, for example, a mirrored surface, a metal-coated surface, or a surface with a film of deposited metal.

The reflector 35 is connected to an inner circumferential surface of the light source housing 31. The reflector 35 reflects light from the light source 34 toward the opening of the light source housing 31. The reflector 35 may include a dielectric film that reflects light with a specific wavelength range. The dielectric film may reflect, for example, light with wavelengths that can contribute to enhancing the cosmetic treatment effect of body hair. The reflector 35 absorbs light in a wavelength range of less than 800 nm, for example. The reflector 35 absorbs light in a wavelength range of 400 nm or greater to less than 800 nm, for example.

The lens 36 has a shape similar to a circle. The lens 36 is formed from a material having high light transmittance in a specific wavelength range. The lens 36 is, for example, formed from a material with high transmittance in a wavelength range of visible light and in a wavelength range of infrared light. The lens 36 is, for example, formed from acrylic, polycarbonate, or glass. The lens 36 is arranged in the internal space of the light source housing 31. The lens 36 is connected to the light source housing 31. The lens 36 diffuses light reflected from the reflector 35 toward the outside of the light source housing 31. The lens 36 can smooth the energy density of light measured at an external position separated from the opening of the light source housing 31 by a predetermined distance (energy density smoothing structure).

The optical filter 37 is formed mainly from glass. The optical filter 37 has a shape similar to a circle. The optical filter 37 is arranged at the opening of the light source housing 31. The optical filter 37 is arranged outward from the light source housing 31 with respect to the lens 36. The optical filter 37 is placed on the lens 36 to cover an outer surface of the lens 36. The optical filter 37 is mechanically connectable to and separable from the filter mounting part 33. The optical filter 37 is mechanically connected to the filter mounting part 33. The optical filter 37 may be a wavelength selective filter that can absorb light with a specific wavelength range. The optical filter 37 is designed to absorb light of a wavelength outside a wavelength range of 800 nm to 1200 nm, for example.

The light absorbing structure of the optical filter 37 may include, for example, a glass base containing a light absorbing material. The optical filter 37 includes a light absorbing film that may be, for example, a metal film, a dielectric film, or a composite film containing metal and dielectric. The metal film may be, for example, a film of titanium oxide, zirconium oxide, or aluminum oxide. Another example of the light absorbing structure includes a glass base having a light absorbing film on its surface. The light absorbing material includes, for example, metal particles or an oxide of metal particles. The metal may be, for example, gold, silver, copper, lead, zinc, cobalt, or manganese. The light absorbing film may have a monolayer or multilayer structure. The multilayer structure of the light absorbing film is formed by, for example, vacuum vapor deposition. The light absorbing structure absorbs light in a wavelength range of less than 800 nm, for example. The light absorbing structure absorbs light in a wavelength range of 400 nm or greater to less than 800 nm, for example.

The light source housing 31, the reflector 35, and the optical filter 37 absorb light in a wavelength range of less than 800 nm. Therefore, compared to a structure in which at least one of the light source housing 31 and reflector 35 does not absorb light, increases in the temperature of the optical filter 37 are more limited.

The cosmetic light for body hair that has passed through the optical filter 37 preferably has only a component included in the wavelength range of 800 nm to 1200 nm. The cosmetic light for body hair that has passed through the optical filter 37 may also include a component outside the wavelength range of 800 nm to 1200 nm. The component outside the wavelength range of 800 nm to 1200 nm is sufficiently small in the amount of optical energy as compared to the component included in the wavelength range of 800 nm to 1200 nm. Therefore, the component outside the wavelength range of 800 nm to 1200 nm have a small, if any, influence on the body hair and skin.

The power supply circuit unit 40 is accommodated in the internal space of the body housing 21. The power supply circuit unit 40 supplies power from a power supply incorporated in the body housing 21 or from an external power supply to the light source 34.

The control unit 50 is accommodated in the internal space of the body housing 21. The control unit 50 controls at least one of a voltage or a current supplied to the light source 34 to control light emitted from the light source 34. For example, the control unit 50 adjusts the total amount of light energy of light emitted from the light source 34 per irradiation, and the time for which light is emitted from the light source 34 per irradiation (hereafter, irradiation time), and/or the energy density of light applied from the light source 34 per irradiation. The irradiation time per irradiation is set in a range of 600 µs to 2 ms. The energy density of light per irradiation is set in a range of 0.2 to 1.5 (J/cm$^2$). The energy density of light is set in accordance with the integral of the spectral irradiance in the selected wavelength range.

Figure 2:
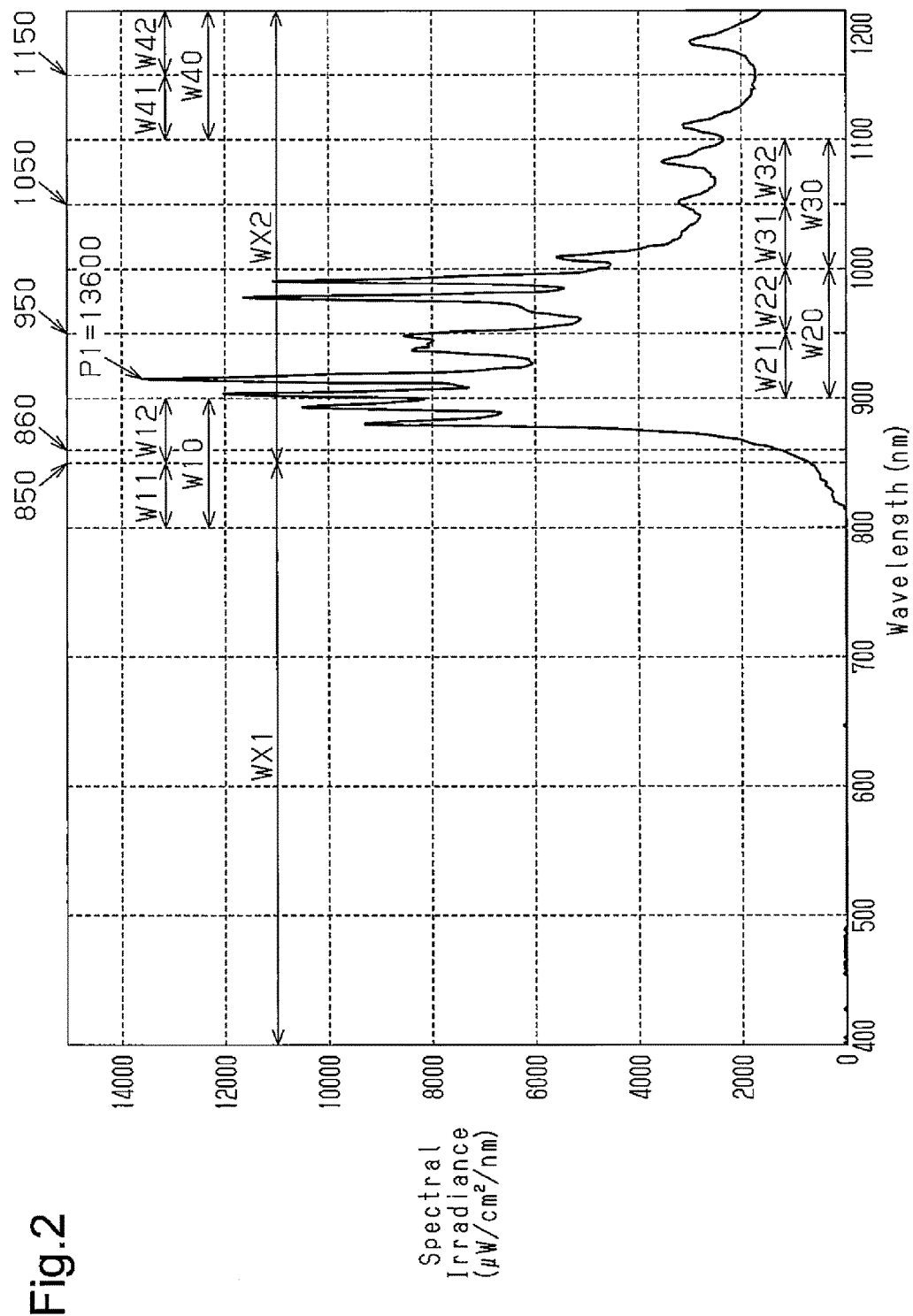
FIG. 2 is a graph showing a light source spectrum for cosmetic light for body hair in the first embodiment.

The cosmetic light for body hair has a light source spectrum as shown in FIG. 2, for example. The light source spectrum of the cosmetic light for body hair is formed when the light emitted from the light source 34 passes through the lens 36 and the optical filter 37.

The inventors of the present application divided the wavelength range of 400 nm to 1200 nm into a plurality of wavelength ranges, and conducted experiments to study the relationship between the optical energy and the body hair cosmetic treatment effect for each of the wavelength ranges. The results of the experiment indicates that the degree for enhancing the body hair cosmetic treatment effect with respect to the amount of optical energy is low for light in the wavelength range of 400 nm to 850 nm as compared to light in the wavelength range of 850 nm to 1200 nm. More specifically, the results of the experiments show that in when light of the above two wavelength ranges are comprehensively compared, the light in the wavelength range of 850 nm to 1200 nm can more effectively enhance the body hair cosmetic treatment effect than the light in the wavelength range of 400 nm to 850 nm.

The inventors of the present application identified the cosmetic light for body hair of FIG. 2 from the above experiment results. The integral of the intensity of the cosmetic light for body hair is smaller in the wavelength range of 400 nm to 850 nm than in the wavelength range of 850 nm to 1200 nm. In this manner, the cosmetic light for body hair has a smaller amount of optical energy in the wavelength range of 400 nm 850 nm than in the wavelength range of 850 nm to 1200 nm. This finding was not known in the field of optical cosmetic devices for body hair prior to the filing of the present application.

The light source spectrum of the cosmetic light for body hair will now described.

The body hair optical cosmetic device 10 defines the intensity of light with a spectral irradiance (µW/cm$^2$/nm) for example. The cosmetic light for body hair has an intensity integral that is larger in the wavelength range of 800 nm to 1200 nm than in the wavelength range of 400 nm to 800 nm. The cosmetic light for body hair has a significant peak in the wavelength range of 800 nm to 1200 nm, and has no significant peaks in a wavelength range that is shorter than 800 nm. When the cosmetic light for body hair is described, a phrase such as "have a peak" is used to indicate that the cosmetic light for body hair has a significant peak. Further, when the cosmetic light for body hair is described, a phrase such as "have no peak" is used to indicate that the cosmetic light for body hair has no significant peak.

The cosmetic light for body hair can be divided into a wavelength component having a level greater than or equal to a certain spectral irradiance and a wavelength component having a level less than the certain spectral irradiance. The wavelength component having a level higher than or equal to the certain spectral irradiance indicates a component considered as having a significant effect on the growth of body hair. The wavelength component having a level lower than the certain spectral irradiance indicates a component considered as having no significant effect on the growth of body hair. A significant peak of the cosmetic light for body hair indicates a peak appearing in the wavelength component having a level greater than or equal to the certain spectral irradiance.

In the description hereafter, the wavelength range of 400 nm to 1200 nm may be divided into a 400 nm to 850 nm range WX1 and an 850 nm to 1200 nm range WX2, in which 850 nm serves as a borderline. The 400 nm to 850 nm range WX1 is a wavelength range of 400 nm or greater to less than 850 nm. The 850 nm to 1200 nm range WX2 is a wavelength range of 850 nm to 1200 nm.

In the following description, the wavelength range of 800 nm to 1200 nm may be divided into four at every 100 nm. The four types of wavelength ranges are an 800 nm to 900 nm range W10, a 900 nm to 1000 nm range W20, a 1000 nm to 1100 nm range W30, and a 1100 nm to 1200 nm range W40.

In the following description, the 800 nm to 900 nm range W10 may be divided into an 800 nm to 850 nm range W11 and an 850 nm to 900 nm range W12. The same applies for the ranges W20, W30 and W40.

The cosmetic light for body hair has a plurality of peaks in a wavelength range of greater than 860 nm to 1200 nm or less. The cosmetic light for body hair has a maximum peak P1 in the 900 nm to 1000 nm range W20. The cosmetic light for body hair has no peaks in the wavelength range of 800 nm to 860 nm. The cosmetic light for body hair has no peaks in the wavelength range of 400 nm or greater to less than 800 nm. The maximum peak P1 has a spectral irradiance of 13600 ($\mu W/cm^2/nm$), for example.

The spectral irradiance of the maximum peak P1 is preferably included within a suitable peak illuminance range. The suitable peak illuminance range is an illuminance range in which a preferable cosmetic treatment enhancement effect can be obtained, and is, for example, in a range of 2700 to 19900 ($\mu W/cm^2/nm$), and preferably, in a range of 9300 to 17300 ($\mu W/cm^2/nm$).

The integral of the spectral irradiance in the 800 nm to 900 nm range W10 is referred to as the integral S10. The integral of the spectral irradiance in the 800 nm to 850 nm range W11 is referred to as the integral S11. The integral of spectral irradiance in the 850 nm to 900 nm range W12 is referred to as the integral S12.

In the same manner, an integral S20 indicates an integral of the spectral irradiance in the 900 nm to 1000 nm range W20. An integral S21 refers to an integral of the spectral irradiance in the 900 nm to 950 nm range W21. An integral S22 refers to an integral of the spectral irradiance in the 950 nm to 1000 nm range W22. An integral S30 refers to an integral of the spectral irradiance in the 1000 nm to 1100 nm range W30. An integral S31 refers to an integral of the spectral irradiance in the 1000 nm to 1050 nm range W31. An integral S32 refers to an integral of the spectral irradiance in the 1050 nm to 1100 nm range W32. An integral S40 refers to an integral of the spectral irradiance in the 1100 nm to 1200 nm range W40. An integral S41 refers to an integral of the spectral irradiance in the 1100 nm to 1150 nm range W41. An integral S42 refers to an integral of the spectral irradiance within the 1150 nm to 1200 nm range W42.

A 400 nm to 850 nm integral SX1 is included in a first suitable integral range. The first suitable integral range is an integral range that is preferable in terms of the side effect inhibition effect, and is, for example, a range of 0.01 to 0.05 ($\mu W/cm^2$), preferably, a range of 0.03 to 0.04 ($\mu W/cm^2$).

An 850 nm to 1200 nm integral SX2 is included in a second suitable integral range. The second suitable integral range is an integral range that can obtain a preferable cosmetic treatment enhancement effect and side effect inhibition effect, and is, for example, a range of 0.19 to 1.45 ($\mu W/cm^2$), preferably, a range of 0.67 to 1.26 ($\mu W/cm^2$).

An 800 nm to 900 nm integral S10 is preferably included in a third suitable integral range. The third suitable integral range is an integral range that can obtain a preferable cosmetic treatment enhancement effect and side effect inhibition effect, and is, for example, a range of 0.03 to 0.21 ($\mu W/cm^2$), preferably, a range of 0.10 to 0.19 ($\mu W/cm^2$).

An 800 nm to 850 nm integral S11 is preferably included in a fourth suitable integral range. The fourth suitable integral range is an integral range that can obtain a preferable cosmetic treatment enhancement effect and side effect inhibition effect, and for example is of a range of 0 to 0.01 ($\mu W/cm^2$), preferably, a range of 0.005 to 0.01 ($\mu W/cm^2$).

An 850 nm to 900 nm integral S12 is preferably included in a fifth suitable integral range. The fifth suitable integral range is an integral that can obtain a preferable cosmetic treatment enhancement effect and side effect inhibition effect, and is, for example, a range of 0.03 to 0.20 ($\mu W/cm^2$), preferably, a range of 0.09 to 0.18 ($\mu W/cm^2$).

A 900 nm to 1000 nm integral S20 is preferably included in a sixth suitable integral range. The sixth suitable integral range is an integral range that can obtain a preferable cosmetic treatment enhancement effect and side effect inhibition effect, and is, for example, a range of 0.09 to 0.68 ($\mu W/cm^2$), preferably, a range of 0.32 to 0.59 ($\mu W/cm^2$).

A 900 nm to 950 nm integral S21 is preferably included in a seventh suitable integral range. The seventh suitable integral range is an integral range that can obtain a preferable cosmetic treatment enhancement effect and side effect inhibition effect, and is, for example, a range of 0.05 to 0.38 ($\mu W/cm^2$), preferably, a range of 0.18 to 0.33 ($\mu W/cm^2$).

A 950 nm to 1000 nm integral S22 is preferably included in an eighth suitable integral range. The eighth appropriate integral is an integral range that can obtain a preferable cosmetic treatment enhancement effect and side effect inhibition effect, and is, for example, a range of 0.04 to 0.31 ($\mu W/cm^2$), preferably, a range of 0.14 to 0.26 ($\mu W/cm^2$).

A 1000 nm to 1100 nm integral S30 is preferably included in a ninth suitable integral range. The ninth suitable integral range is an integral range that can obtain a preferable cosmetic treatment enhancement effect and side effect inhibition effect, and is, for example, a range of 0.04 to 0.29 ($\mu W/cm^2$), preferably, a range of 0.14 to 0.25 ($\mu W/cm^2$).

A 1000 nm to 1050 nm integral S31 preferably is included in a tenth suitable integral range. The tenth suitable integral range is an integral range that can obtain a preferable cosmetic treatment enhancement effect and side effect inhibition effect, and is, for example, a range of 0.02 to 0.17 ($\mu W/cm^2$), preferably, a range of 0.08 to 0.15 ($\mu W/cm^2$).

A 1050 nm to 1100 nm integral S32 preferably is included in an eleventh suitable integral range. The eleventh suitable integral range is an integral range that can obtain a preferable cosmetic treatment enhancement effect and side effect inhibition effect, and is, for example, a range of 0.02 to 0.13 ($\mu W/cm^2$), preferably, a range of 0.06 to 0.11 ($\mu W/cm^2$).

A 1100 nm to 1200 nm integral S40 is preferably included in a twelfth suitable integral range. The twelfth suitable integral range is an integral range that can obtain a preferable cosmetic treatment enhancement effect and side effect inhibition effect, and is, for example, a range of 0.03 to 0.20 ($\mu W/cm^2$), preferably, a range of 0.09 to 0.17 ($\mu W/cm^2$).

A 1100 nm to 1150 nm integral S41 is preferably included in a thirteenth suitable integral range. The thirteenth integral range is an integral range that can obtain a preferable cosmetic treatment enhancement effect and side effect inhibition effect, and is, for example, a range of 0.01 to 0.10 ($\mu W/cm^2$), preferably, a range of 0.05 to 0.09 ($\mu W/cm^2$).

A 1150 nm to 1200 nm integral S42 is preferably included in a fourteenth suitable integral range. The fourteenth suitable integral range is an integral range that can obtain a preferable cosmetic treatment enhancement effect and side effect inhibition effect, and is, for example, a range of 0.01 to 0.10 ($\mu W/cm^2$), preferably, a range of 0.05 to 0.08 ($\mu W/cm^2$).

The integrals have the following relationships.

The integral SX1 is smaller than a total value of the integrals S12, S20, S30, and S40. More specifically, the amount of optical energy in the wavelength range of 400 nm to 850 nm is smaller than the amount of optical energy in the wavelength range of 850 nm to 1200 nm.

The integral SX1 is smaller than a total value of the integrals S20, S30, and S40. More specifically, the amount of optical energy in the wavelength range of 400 nm to 850 nm is smaller than the amount of optical energy in the wavelength range of 900 nm to 1200 nm.

The integral SX1 is smaller than a total value of the integrals S22, S30, and S40. More specifically, the amount of optical energy in the wavelength range of 400 nm to 850 nm is smaller than the amount of optical energy in the wavelength range of 950 nm to 1200 nm.

The integral SX1 is smaller than a total value of the integrals S30 and S40. More specifically, the amount of optical energy in the wavelength range of 400 nm to 850 nm is smaller than the amount of optical energy in the wavelength range of 1000 nm to 1200 nm.

The integral SX1 is smaller than a total value of the integrals S32 and S40. More specifically, the amount of optical energy in the wavelength range of 400 nm to 850 nm is smaller than the amount of optical energy in the wavelength range of 1050 nm to 1200 nm.

The integral SX1 is smaller than the integral S10. More specifically, the amount of optical energy in the wavelength range of 400 nm to 850 nm is smaller than the amount of optical energy in the wavelength range of 800 nm to 900 nm.

The integral SX1 is smaller than the integral S12. More specifically, the amount of optical energy in the wavelength range of 400 nm to 850 nm is smaller than the amount of optical energy in the wavelength range of 850 nm to 900 nm.

The integral SX1 is smaller than the integral S20. More specifically, the amount of optical energy in the wavelength range of 400 nm to 850 nm is smaller than the amount of optical energy in the wavelength range of 900 nm to 1000 nm.

The integral SX1 is smaller than the integral S21. More specifically, the amount of optical energy in the wavelength range of 400 nm to 850 nm is smaller than the amount of optical energy in the wavelength range of 900 nm to 950 nm.

The integral SX1 is smaller than the integral S22. More specifically, the amount of optical energy in the wavelength range of 400 nm to 850 nm is smaller than the amount of optical energy in the wavelength range of 950 nm to 1000 nm.

The integral SX1 is smaller than the integral S30. More specifically, the amount of optical energy in the wavelength range of 400 nm to 850 nm is smaller than the amount of optical energy in the wavelength range of 1000 nm to 1100 nm.

The integral SX1 is smaller than the integral S31. More specifically, the amount of optical energy in the wavelength range of 400 nm to 850 nm is smaller than the optical energy in the wavelength range of 1000 nm to 1050 nm.

The integral SX1 is smaller than the integral S32. More specifically, the amount of optical energy in the wavelength range of 400 nm to 850 nm is smaller than the amount of optical energy in the wavelength range of 1050 nm to 1100 nm.

The integral SX1 is smaller than the integral S40. More specifically, the amount of optical energy in the wavelength range of 400 nm to 850 nm is smaller than the amount of optical energy in the wavelength range of 1100 nm to 1200 nm.

The integral SX1 is smaller than the integral S41. More specifically, the amount of optical energy in the wavelength range of 400 nm to 850 nm is smaller than the amount of optical energy in a wavelength range of 1100 nm to 1150 nm.

The integral SX1 is smaller than the integral S42. More specifically, the amount of optical energy in the wavelength range of 400 nm to 850 nm is smaller than the amount of optical energy in the wavelength range of 1150 nm to 1200 nm.

A total value of the integrals S10 and S20 is greater than the total value of the integrals S30 and S40. More specifically, the amount of optical energy in the wavelength range of 800 nm to 1000 nm is greater than the amount of optical energy in the wavelength range of 1000 nm to 1200 nm.

A total value of the integrals S12 and S20 is greater than the total value of the integrals S30 and S40. More specifically, the amount of optical energy in the wavelength range of 850 nm to 1000 nm is greater than the optical energy in the wavelength range of 1000 nm to 1200 nm.

The integral S20 is greater than the total value of the integrals S30 and S40. More specifically, the amount of optical energy in the wavelength range of 900 nm to 1000 nm is greater than the amount of optical energy in the wavelength range of 1000 nm to 1200 nm.

The integral S20 is greater than the integral S40. More specifically, the amount of optical energy in the wavelength range of 900 nm to 1000 nm is greater than the amount of optical energy in the wavelength range of 1100 nm to 1200 nm.

The integral S30 is greater than the integral S40. More specifically, the amount of optical energy in the wavelength range of 1000 nm to 1100 nm is greater than the amount of optical energy in the wavelength range of 1100 nm to 1200 nm.

The integral S12 is greater than the integral S40. More specifically, the amount of optical energy in the wavelength range of 850 nm to 900 nm is greater than the amount of optical energy in the wavelength range of 1100 nm to 1200 nm.

The integral S21 is greater than the integral S40. More specifically, the amount of optical energy in the wavelength range of 900 nm to 950 nm is greater than the amount of optical energy in the wavelength range of 1100 nm to 1200 nm.

The integral S22 is greater than the integral S40. More specifically, the amount of optical energy in the wavelength range of 950 nm to 1000 nm is greater than the amount of optical energy in the wavelength range of 1100 nm to 1200 nm.

The body hair optical cosmetic device 10 has the following advantages.

(1) The body hair optical cosmetic device 10 includes an optical system that emits cosmetic light for body hair, and the intensity integral is larger in the wavelength range of 800 nm to 1200 nm than in the wavelength range of 400 nm to 800 nm. The inventors of the present application confirmed through experimentation that by using cosmetic light for body hair having this feature, the following effect is obtained. The cosmetic light for body hair enhances the body hair cosmetic treatment effect and inhibits the growth of body hair.

The reason why the body hair cosmetic treatment effect is easily enhanced is considered to be as follows.

A living body has light absorbing components other than melanin and oxygenated hemoglobin. Many of the other light absorbing components exist deep inside the living body rather than near the epidermis. Melanin is classified a melanin that exists at a region close to the epidermis and melanin that exists within a deep region of the living body. More specifically, the light absorbing components existing inside the living body can be classified into a component existing near the epidermis of the living body and a component existing deep in the living body. A component existing near the epidermis mainly contains melanin and oxygenated hemoglobin. A component existing deep in the living body mainly contains melanin and other light absorbing components.

The light absorbing component existing deep part in a living body greatly affects the enhancement of the body hair cosmetic treatment effect. Therefore, the body hair cosmetic treatment effect can easily be enhanced when light absorbing components existing deep in the living body absorbs more light.

Light enters a living body to different depths depending on its wavelength. Light of a long wavelength cannot be easily absorbed by the light absorbing component existing near the epidermis as compared to light of a short wavelength. Light with a long wavelength can reach deep into a living body more easily as compared to light with a short wavelength. Therefore, light in the wavelength range of 800 nm to 1200 nm, for example, is more easily absorbed by the light absorbing component existing deep in a living body as compared to light in a wavelength range of 400 nm to 800 nm.

The cosmetic light for body hair has a large intensity integral in the wavelength range of 800 nm to 1200 nm that is easily absorbed by the light absorbing component existing deep in the living body. Therefore, the cosmetic light for body hair applies a large amount of optical energy to the light absorbing components. This allows for the body hair cosmetic treatment effect to be easily enhanced. The light in the wavelength range of 800 nm to 1200 nm cannot be easily absorbed by the light absorbing component existing near the epidermis. Therefore, the cosmetic light for body hair does not easily affect the skin.

(2) The cosmetic light for body hair has an intensity integral that is smaller in the wavelength range of 400 nm to 850 nm than in a wavelength range of 850 nm to 1200 nm. The inventors of the present application confirmed through experimentation that by using the cosmetic light for body hair that has this feature, the following effect is obtained. The cosmetic light for body hair effectively enhances the body hair cosmetic treatment effect as compared to when the intensity integral is larger in the wavelength range of 400 nm to 850 nm than in the wavelength range of 850 nm to 1200 nm.

The reason why the body hair cosmetic treatment effect is effectively enhanced is considered to be as follows.

The light in the wavelength range of 850 nm to 1200 nm can be more easily absorbed by the light absorbing component existing deep in the living body than the light in the wavelength range of 400 nm to 850 nm for the same reasons as described in advantage (1). Therefore, when an absorbance integral is larger in the wavelength range of 850 nm to 1200 nm than in the wavelength range of 400 nm to 850 nm, the light absorbing component existing deep in the living body can receive more optical energy from the light. Accordingly, the cosmetic light for body hair effectively enhances the body hair cosmetic treatment effect. The absorbance integral is obtained by integrating absorbance with wavelength in the light source spectrum of the light absorbing component.

(3) The cosmetic light for body hair has the feature of the advantage (2). The inventors of the present application confirmed through experimentation that by using the cosmetic light for body hair having this feature, the following effect can be obtained. The cosmetic light for body hair exhibits an excellent side effect inhibition effect as compared to when the intensity integral is larger in the wavelength range of 400 nm to 850 nm than in the wavelength range of 850 nm to 1200 nm.

The reason why an excellent side effect inhibition effect is obtained is considered to be as follows.

Oxygenated hemoglobin has an absorbance peak in a wavelength range of 400 nm to 600 nm. Therefore, a large amount of optical energy in the wavelength range of 400 nm to 600 nm increases the amount of optical energy absorbed by the oxygenated hemoglobin. Accordingly, there is an increased risk in the occurrence of an unwanted side effect for the skin.

The inventors of the present application conducted experiments related to the absorptivity of eumelanin and pheomelanin and obtained the following results. Eumelanin has a high absorptivity in the wavelength range of 400 nm to 1200 nm. Pheomelanin has a high absorptivity in the wavelength range of 400 nm to 700 nm. In the wavelength range of 400 nm to 700 nm, the absorptivity of pheomelanin further increases as the wavelength becomes shorter. Therefore, a large amount of optical energy in the wavelength range of 400 nm to 700 nm increases the amount of optical energy absorbed by both of the eumelanin and pheomelanin. This increases the risk of occurrence of an unwanted side effect for the skin.

The cosmetic light for body hair has a relatively small amount of optical energy in a wavelength range that allows for easy absorption of light by the oxygenated hemoglobin and melanin. Therefore, the cosmetic light for body hair obtains an excellent side effect inhibition effect.

(4) The body hair optical cosmetic device 10 also obtains advantages (1) to (3). More specifically, the body hair optical cosmetic device 10 can inhibit the growth of body hair while preventing unwanted side effects on the skin.

(5) The cosmetic light for body hair has an intensity integral that is smaller in the wavelength range of 400 nm to 850 nm than in the wavelength range of 900 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in a wavelength range of 400 nm to 850 nm than in a wavelength range of 900 nm to 1200 nm.

(6) The cosmetic light for body hair has an intensity integral that is smaller in the wavelength range of 400 nm to 850 nm than in the wavelength range of 950 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than the intensity integral in a wavelength range of 950 nm to 1200 nm.

(7) The cosmetic light for body hair has an intensity integral that is smaller in the wavelength range of 400 nm to 850 nm than in the wavelength range of 1000 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in a wavelength range of 400 nm to 850 nm is greater than the intensity integral in the wavelength range of 1000 nm to 1200 nm.

(8) The cosmetic light for body hair has an intensity integral that is smaller in a wavelength range of 400 nm to 850 nm than in the wavelength range of 1050 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1050 nm to 1200 nm.

(9) The cosmetic light for body hair has an intensity integral that is smaller in the wavelength range of 400 nm to 850 nm than in the wavelength range of 800 nm to 900 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 800 nm to 900 nm.

(10) The cosmetic light for body hair has an intensity integral that is smaller in the wavelength range of 400 nm to 850 nm than in the wavelength range of 850 nm to 900 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 850 nm to 900 nm.

(11) The cosmetic light for body hair has an intensity integral is smaller in the wavelength range of 400 nm to 850 nm than in a wavelength range of 900 nm to 1000 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 900 nm to 1000 nm.

(12) The cosmetic light for body hair has an intensity integral that is smaller in the wavelength range of 400 nm to 850 nm than in the wavelength range of 900 nm to 950 nm. The inventors of the present application confirmed through experimentation that the cosmetic light for body hair having this feature can obtain the following effect. The cosmetic light for body hair obtains a preferable cosmetic treatment enhancement effect and side effect inhibition effect in when the intensity integral is larger in the wavelength range of 400 nm to 850 nm than in the wavelength range of 900 nm to 950 nm.

(13) The cosmetic light for body hair has an intensity integral that is smaller in the wavelength range of 400 nm to 850 nm than in the wavelength range of 950 nm to 1000 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 950 nm to 1000 nm.

(14) The cosmetic light for body hair has an intensity integral that is smaller in the wavelength range of 400 nm to 850 nm than in the wavelength range of 1000 nm to 1100 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1000 nm to 1100 nm.

(15) The cosmetic light for body hair has an intensity integral that is smaller in the wavelength range of 400 nm to 850 nm than in the wavelength range of 1000 nm to 1050 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1000 nm to 1050 nm.

(16) The cosmetic light for body hair has an intensity integral that is smaller in the wavelength range of 400 nm to 850 nm than in the wavelength range of 1050 nm to 1100 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1050 nm to 1100 nm.

(17) The cosmetic light for body hair has an intensity integral that is smaller in the wavelength range of 400 nm to 850 nm than in the wavelength range of 1100 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1100 nm to 1200 nm.

(18) The cosmetic light for body hair has an intensity integral that is smaller in the wavelength range of 400 nm to 850 nm than in the wavelength range of 1100 nm to 1150 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1100 nm to 1150 nm.

(19) The cosmetic light for body hair has an intensity integral that is smaller in the wavelength range of 400 nm to 850 nm than in the wavelength range of 1150 nm to 1200 nm. The inventors of the present application confirmed through experimentation that the cosmetic light of body hair having this feature can obtain the following effect. The cosmetic light for body hair obtains a preferable cosmetic treatment enhancement effect and side effect inhibition effect as compared to when the intensity integral is larger in the wavelength range of 400 nm to 850 nm than in the wavelength range of 1150 nm to 1200 nm.

(20) The cosmetic light for body hair has an intensity integral that is larger in the wavelength range of 800 nm to 1000 nm than in the wavelength range of 1000 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 800 nm to 1000 nm is smaller than the intensity integral in the wavelength range of 1000 nm to 1200 nm.

(21) The cosmetic light for body hair has an intensity integral that is larger in the wavelength range of 850 nm to 1000 nm than in the wavelength range of 1000 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 850 nm to 1000 nm is smaller than the intensity integral in the wavelength range of 1000 nm to 1200 nm.

(22) The cosmetic light for body hair has an intensity integral that is larger in the wavelength range of 900 nm to 1000 nm than in the wavelength range of 1000 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 900 nm to 1000 nm is smaller than the intensity integral in the wavelength range of 1000 nm to 1200 nm.

(23) The cosmetic light for body hair has an intensity integral that is larger in the wavelength range of 900 nm to 1000 nm than in the wavelength range of 1100 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 900 nm to 1000 nm is smaller than the intensity integral in the wavelength range of 1100 nm to 1200 nm.

(24) The cosmetic light for body hair has an intensity integral that is larger in the wavelength range of 1000 nm to 1100 nm than in the wavelength range of 1100 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 1000 nm to 1100 nm is smaller than the intensity integral in the wavelength range of 1100 nm to 1200 nm.

(25) The cosmetic light for body hair has an intensity integral that is larger in the wavelength range of 850 nm to 900 nm than in the wavelength range of 1100 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 850 nm to 900 nm is smaller than the intensity integral in the wavelength range of 1100 nm to 1200 nm.

(26) The cosmetic light for body hair has an intensity integral that is larger in the wavelength range of 900 nm to 950 nm than in the wavelength range of 1100 nm to 1200 nm. The inventors of the present application confirmed through experimentation that the cosmetic light of body hair having this feature can obtain the following effect. The cosmetic light for body hair obtains a preferable cosmetic treatment enhancement effect and side effect inhibition effect as compared to when the intensity integral in the wavelength range of 900 nm to 950 nm is smaller than the intensity integral in the wavelength range of 1100 nm to 1200 nm.

(27) The cosmetic light for body hair has an intensity integral that is greater in the wavelength range of 950 nm to 1000 nm than in the wavelength range of 1100 nm to 1200 nm. The inventors of the present application confirmed through experimentation that the cosmetic light for body hair having this feature can obtain the following effect. The cosmetic light for body hair obtains a preferable cosmetic treatment enhancement effect and side effect inhibition effect as compared to when the intensity integral in the wavelength range of 950 nm to 1000 nm is smaller than the intensity integral in the wavelength range of 1100 nm to 1200 nm.

(28) The cosmetic light for body hair has an energy density in a range of 0.2 to 1.5 ($J/cm^2$). The inventors of the present application confirmed through experimentation that the cosmetic light for body hair having this feature can obtain the following effect. The cosmetic light for body hair enhances the effect of allowing easy promotion of the body hair cosmetic treatment effect as compared to when the energy density is less than 0.2 ($J/cm^2$). The cosmetic light for body hair does not easily cause an unwanted side effect for the skin as compared to when the energy density is greater than 1.5 ($J/cm^2$).

(29) The irradiation time of the cosmetic light for body hair is in a range of 600 μs to 2 ms per irradiation. The inventors of the present application confirmed through experimentation that the cosmetic light for body hair having this feature can obtain the following effect. The cosmetic light for body hair enhances the effect of allowing easy enhancement of the body hair cosmetic treatment effect as compared to when the irradiation time is less than 600 μs. The cosmetic light for body hair does not easily cause the occurrence of an unwanted side effect for the skin as compared to when the irradiation time is longer than 2 ms.

Second Embodiment

Figure 3:
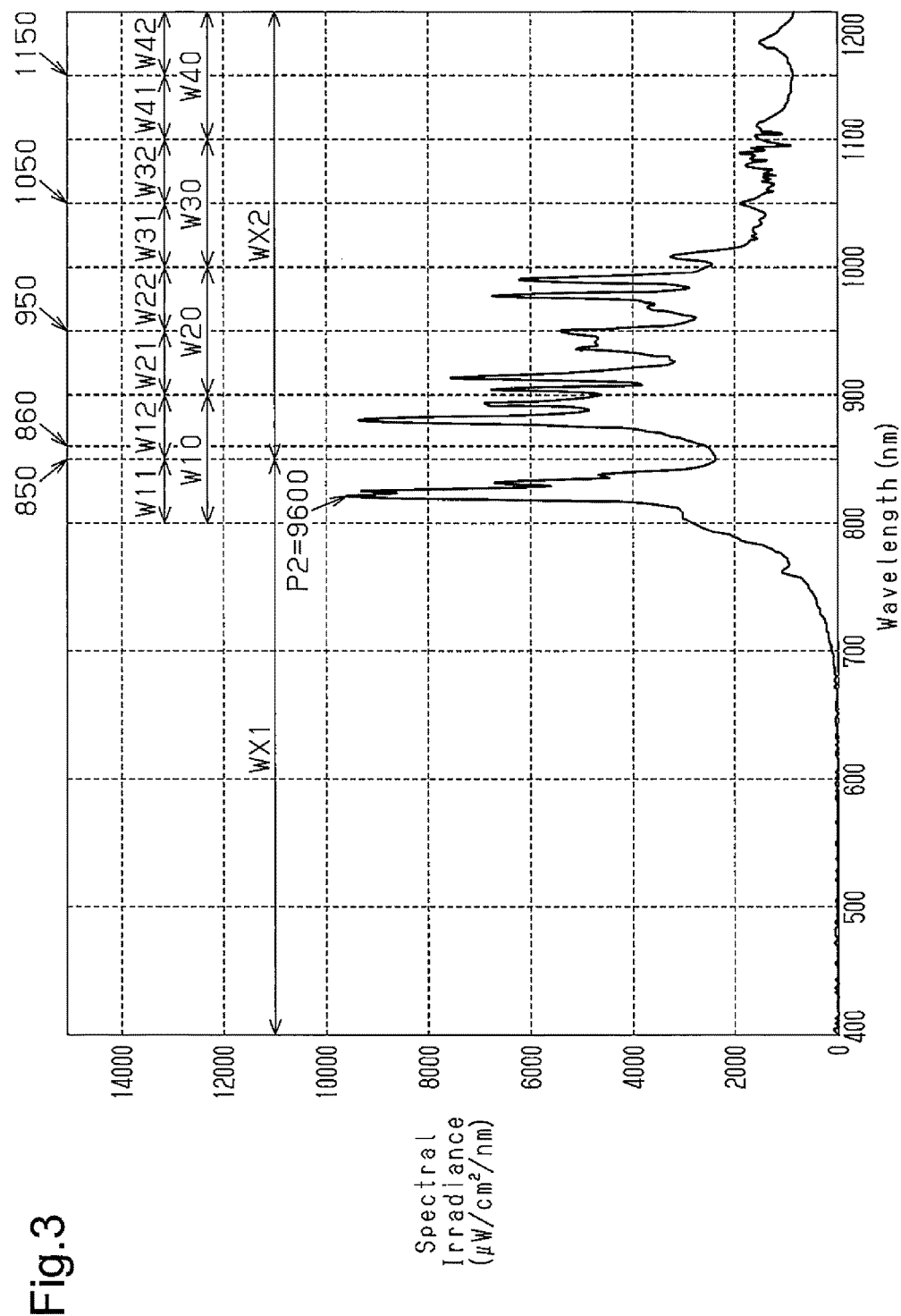
FIG. 3 is a graph showing a light source spectrum of cosmetic light for body hair in a second embodiment.

A body hair optical cosmetic device 10 of a second embodiment differs from the first embodiment in that cosmetic light for body hair having a light source spectrum of FIG. 3 is emitted.

The cosmetic light for body hair has a plurality of peaks in the wavelength range of 800 nm to 1200 nm. The cosmetic light for body hair has a maximum peak P2 in the 800 nm to 900 nm range W10. The maximum peak P2 has a spectral irradiance of 9600 ($μW/cm^2/nm$), for example.

The spectral irradiance of the maximum peak P2 is preferably included in a suitable peak illuminance range.

The suitable peak illuminance range is an illuminance range that can obtain a preferable cosmetic treatment enhancement effect, and is, for example, a range of 2000 to 14700 ($\mu$W/cm$^2$/nm), preferably, a range of 6900 to 12800 ($\mu$W/cm$^2$/nm).

The integrals have the following levels.

(a) The 400 nm to 850 nm integral SX1 is included in the first suitable integral range.

(b) The 850 nm to 1200 nm integral SX2 is included in the second suitable integral range.

(c) The 800 nm to 900 nm integral S10 is included in the third suitable integral range.

(d) The 800 nm to 850 nm integral S11 is included in the fourth suitable integral range.

(e) The 850 nm to 900 nm integral S12 is included in the fifth suitable integral range.

(f) The 900 nm to 1000 nm integral S20 is included in the sixth suitable integral range.

(g) The 900 nm to 950 nm integral S21 is included in the seventh suitable integral range.

(h) The 950 nm to 1000 nm integral S22 is included in the eighth suitable integral range.

(i) The 1000 nm to 1100 nm integral S30 is included in the ninth suitable integral range.

(j) The 1000 nm to 1050 nm integral S31 is included in the tenth suitable integral range.

(k) The 1050 nm to 1100 nm integral S32 is included in the eleventh suitable integral range.

(l) The 1100 nm to 1200 nm integral S40 is included in the twelfth suitable integral range.

(m) The 1100 nm to 1150 nm integral S41 is included in the thirteenth suitable integral range.

(n) The 1150 nm to 1200 nm integral S42 is included in the fourteenth suitable integral range.

The integrals have the following relationships.

The integral SX1 is smaller than a total value of the integrals S12, S20, S30 and S40. More specifically, the amount of optical energy in the wavelength range of 400 nm to 850 nm is smaller than the amount of optical energy in the wavelength range of 850 nm to 1200 nm.

The integral SX1 is smaller than a total value of the integrals S20, S30 and S40. More specifically, the amount of optical energy in the wavelength range of 400 nm to 850 nm is smaller than the amount of optical energy in the wavelength range of 900 nm to 1200 nm.

The integral SX1 is smaller than a total value of the integrals S22, S30 and S40. More specifically, the amount of optical energy in the wavelength range of 400 nm to 850 nm is smaller than the amount of optical energy in the wavelength range of 950 nm to 1200 nm.

The integral SX1 is smaller than the integral S10. More specifically, the amount of optical energy in the wavelength range of 400 nm to 850 nm is smaller than the amount of optical energy in the wavelength range of 800 nm to 900 nm.

The integral SX1 is smaller than the integral S20. More specifically, the amount of optical energy in the wavelength range of 400 nm to 850 nm is smaller than the amount of optical energy in the wavelength range of 900 nm to 1000 nm.

The total value of the integrals S10 and S20 is greater than the total value of the integrals S30 and S40. More specifically, the amount of optical energy in the wavelength range of 800 nm to 1000 nm is greater than the amount of optical energy in the wavelength range of 1000 nm to 1200 nm.

The total value of the integrals S12 and S20 is greater than the total value of the integrals S30 and S40. More specifically, the amount of optical energy in the wavelength range of 850 nm to 1000 nm is greater than the amount of optical energy in the wavelength range of 1000 nm to 1200 nm.

The integral S20 is greater than the total value of the integrals S30 and S40. More specifically, the amount of optical energy in the wavelength range of 900 nm to 1000 nm is greater than the amount of optical energy in the wavelength range of 1000 nm to 1200 nm.

The integral S20 is greater than the integral S40. More specifically, the amount of optical energy in the wavelength range of 900 nm to 1000 nm is greater than the amount of optical energy in the wavelength range of 1100 nm to 1200 nm.

The integral S30 is greater than the integral S40. More specifically, the amount of optical energy in the wavelength range of 1000 nm to 1100 nm is greater than the amount of optical energy in the wavelength range of 1100 nm to 1200 nm.

The integral S12 is greater than the integral S40. More specifically, the amount of optical energy in the wavelength range of 850 nm to 900 nm is greater than the amount of optical energy in the wavelength range of 1100 nm to 1200 nm.

The integral S21 is greater than the integral S40. More specifically, the amount of optical energy in the wavelength range of 900 nm to 950 nm is greater than the optical energy in the wavelength range of 1100 nm to 1200 nm.

The integral S22 is greater than the integral S40. More specifically, the amount of optical energy in the wavelength range of 950 nm to 1000 nm is greater than the amount of optical energy in the wavelength range of 1100 nm to 1200 nm.

A subtracted value obtained by subtracting the integral S11 from the integral SX1 is smaller than each of the integrals S10, S20, S30 and S40. More specifically, the amount of optical energy in the wavelength range of 400 nm to 800 nm is smaller than the amount of optical energy in each of the four wavelength ranges having a 100 nm width in the wavelength ranges from 800 nm to 1200 nm.

The subtracted value obtained by subtracting the integral S11 from the integral SX1 is smaller than each of the integrals S12, S21 and S22. More specifically, the amount of optical energy in the wavelength range of 400 nm to 800 nm is smaller than the amount of optical energy in each of the three wavelength ranges having a 50 nm width in the wavelength range of 850 nm to 1000 nm.

The body hair optical cosmetic device 10 of the second embodiment obtains advantages (1) to (6), (9), (11), and (20) to (29) of the body hair optical cosmetic device 10 of the first embodiment. More specifically, the advantages of effectively enhancement of the body hair cosmetic treatment effect, an excellent side effect inhibition effect, and a variety of other effects are obtained.

Third Embodiment

Figure 4:
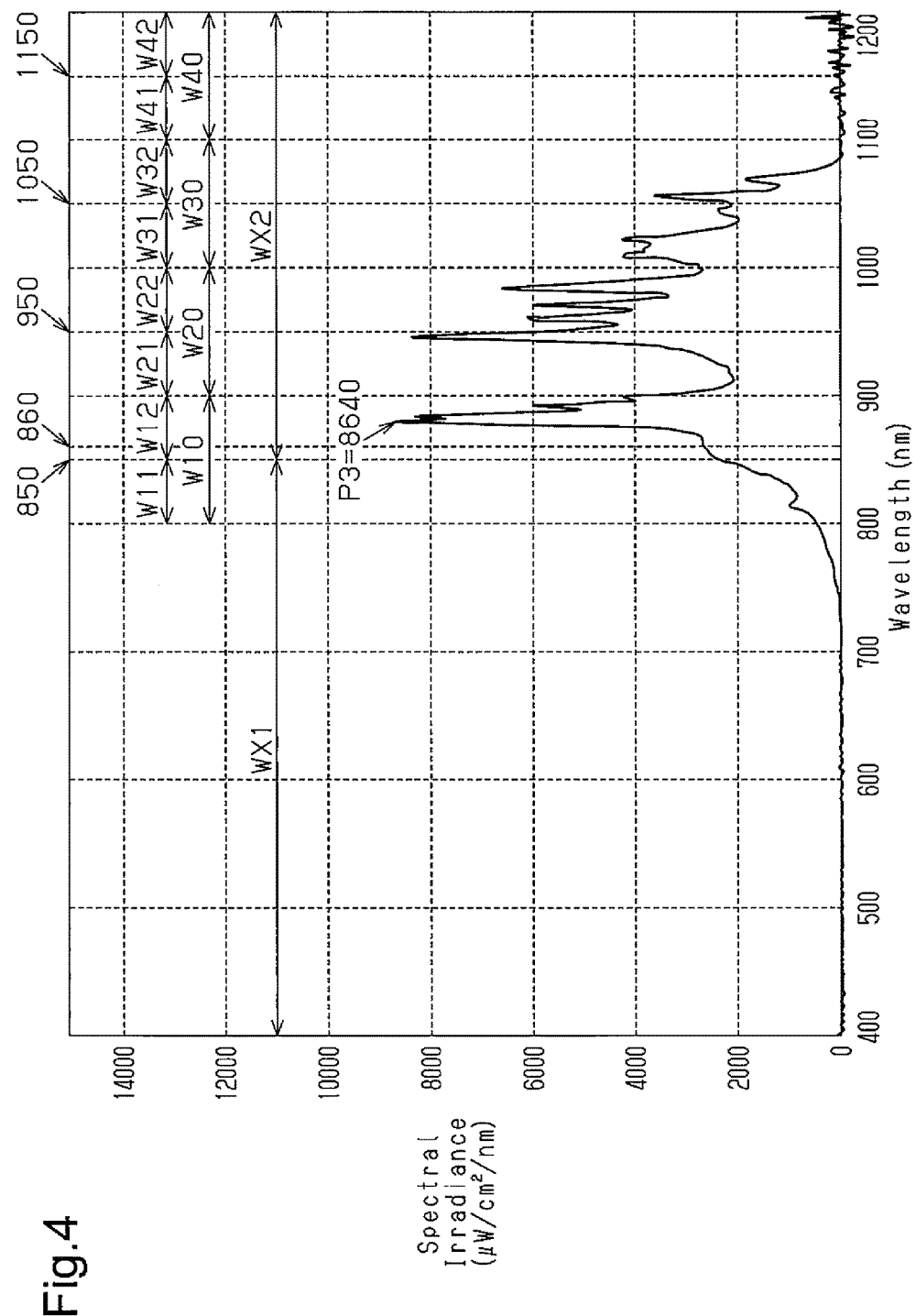
FIG. 4 is a graph showing a light source spectrum of cosmetic light for body hair in a third embodiment.

A body hair optical cosmetic device 10 of a third embodiment differs from the first embodiment in that cosmetic light for body hair having a light source spectrum of FIG. 4 is emitted.

The cosmetic light for body hair of a third embodiment will now be described.

The cosmetic light for body hair has a plurality of peaks in the wavelength range of 850 nm to 1200 nm. The cosmetic light for body hair has a maximum peak P3 in the 800 nm to 900 nm range W10. The maximum peak P3 has a spectral irradiance of 8640 ($\mu$W/cm$^2$/nm), for example.

The spectral irradiance of the maximum peak P3 is preferably included in the suitable peak illuminance range. The suitable peak illuminance range is an illuminance range in which a preferable cosmetic treatment enhancement effect can be obtained, and is, for example, a range of 2100 to 16100 ($\mu W/cm^2/nm$), preferably, a range of 7500 to 13900 ($\mu W/cm^2/nm$).

The integrals have the following levels.

(a) The 400 nm to 850 nm integral SX1 is included in the first suitable integral range.

(b) The 850 nm to 1200 nm integral SX2 is included in the second suitable integral range.

(c) The integral S10 is included in the third suitable integral range.

(d) The 800 nm to 850 nm integral S11 is included in the fourth suitable integral range.

(e) The 850 nm to 900 nm integral S12 is included in the fifth suitable integral range.

(f) The integral S20 is included in the sixth suitable integral range.

(g) The 900 nm to 950 nm integral S21 is included in the seventh suitable integral range.

(h) The 950 nm to 1000 nm integral S22 is included in the eighth suitable integral range.

(i) The 1000 nm to 1100 nm integral S30 is included in the ninth suitable integral range.

(j) The 1000 nm to 1050 nm integral S31 is included in the tenth suitable integral range.

The integrals have the following relationships.

The integral SX1 is smaller than the total value of the integrals S12, S20, S30 and S40. More specifically, the amount of optical energy in the wavelength range of 400 nm to 850 nm is smaller than the amount of optical energy in the wavelength range of 850 nm to 1200 nm.

The integral SX1 is smaller than the total value of the integrals S20 and S30. More specifically, the amount of optical energy in the wavelength range of 400 nm to 850 nm is smaller than the amount of optical energy in the wavelength range of 900 nm to 1100 nm.

The integral SX1 is smaller than the total value of the integrals S22 and S30. More specifically, the amount of optical energy in the wavelength range of 400 nm to 850 nm is smaller than the amount of optical energy in the wavelength range of 950 nm to 1100 nm.

The integral SX1 is smaller than the integral S10. More specifically, the amount of optical energy in the wavelength range of 400 nm to 850 nm is smaller than the amount of optical energy in the wavelength range of 800 nm to 900 nm.

The integral SX1 is smaller than the integral S12. More specifically, the amount of optical energy in the wavelength range of 400 nm to 850 nm is smaller than the amount of optical energy in the wavelength range of 850 nm to 900 nm.

The integral SX1 is smaller than the integral S20. More specifically, the amount of optical energy in the wavelength range of 400 nm to 850 nm is smaller than the amount of optical energy in the wavelength range of 900 nm to 1000 nm.

The integral SX1 is smaller than the integral S21. More specifically, the amount of optical energy in the wavelength range of 400 nm to 850 nm is smaller than the amount of optical energy in the wavelength range of 900 nm to 950 nm.

The integral SX1 is smaller than the integral S22. More specifically, the amount of optical energy in the wavelength range of 400 nm to 850 nm is smaller than the optical energy in the wavelength range of 950 nm to 1000 nm.

The integral SX1 is smaller than the integral S30. More specifically, the amount of optical energy in the wavelength range of 400 nm to 850 nm is smaller than the amount of optical energy in the wavelength range of 1000 nm to 1100 nm.

The integral SX1 is smaller than the integral S31. More specifically, the amount of optical energy in the wavelength range of 400 nm to 850 nm is smaller than the amount of optical energy in the wavelength range of 1000 nm to 1050 nm.

The total value of the integrals S10 and S20 is greater than the total value of the integrals S30 and S40. More specifically, the amount of optical energy in the wavelength range of 800 nm to 1000 nm is greater than the amount of optical energy in the wavelength range of 1000 nm to 1200 nm.

The total value of the integrals S12 and S20 is greater than the total value of the integrals S30 and S40. More specifically, the amount of optical energy in the wavelength range of 850 nm to 1000 nm is greater than the amount of optical energy of intensity in the wavelength range of 1000 nm to 1200 nm.

The integral S20 is greater than the total value of the integrals S30 and S40. More specifically, the amount of optical energy in the wavelength range of 900 nm to 1000 nm is greater than the amount of optical energy in the wavelength range of 1000 nm to 1200 nm.

The integral S20 is greater than the integral S40. More specifically, the amount of optical energy in the wavelength range of 900 nm to 1000 nm is greater than the optical energy in the wavelength range of 1100 nm to 1200 nm.

The integral S30 is greater than the integral S40. More specifically, the amount of optical energy in the wavelength range of 1000 nm to 1100 nm is greater than the amount of optical energy in the wavelength range of 1100 nm to 1200 nm.

The integral S12 is greater than the integral S40. More specifically, the amount of optical energy in the wavelength range of 850 nm to 900 nm is greater than the amount of optical energy in the wavelength range of 1100 nm to 1200 nm.

The integral S21 is greater than the integral S40. More specifically, the amount of optical energy in the wavelength range of 900 nm to 950 nm is greater than the amount of optical energy in the wavelength range of 1100 nm to 1200 nm.

The integral S22 is greater than the integral S40. More specifically, the amount of optical energy in the wavelength range of 950 nm to 1000 nm is greater than the amount of optical energy in the wavelength range of 1100 nm to 1200 nm.

The body hair optical cosmetic device 10 of the third embodiment obtains advantages (1) to (4), (9) to (15), and (20) to (29) of the body hair optical cosmetic device 10 of the first embodiment. More specifically, effective enhancement of the body hair cosmetic treatment effect, excellent side effect inhibition effect, and a variety of other effects are obtained. In addition, the body hair optical cosmetic device 10 of the third embodiment has the following advantages.

(30) The cosmetic light for body hair has the following feature in addition to advantages (1) to (3) of the first embodiment. The cosmetic light for body hair has a smaller intensity integral in the wavelength range of 400 nm to 850 nm than in the wavelength range of 900 nm to 1100 nm. The inventors of the present application confirmed through experimentation that the cosmetic light for body hair having this feature can obtain the following advantage. The cosmetic light for body hair obtains a preferable cosmetic treatment enhancement effect and side effect inhibition effect as compared to when the intensity integral is larger in the wavelength range of 400 nm to 850 nm than in the wavelength range of 900 nm to 1100 nm.

(31) The cosmetic light for body hair has the following feature in addition to advantages (1) to (3) of the first embodiment. The cosmetic light for body hair has a smaller intensity integral in the wavelength range of 400 nm to 850 nm than in the wavelength range of 950 nm to 1100 nm. The inventors of the present application confirmed through experimentation that the cosmetic light for body hair having this feature can obtain the following advantage. The cosmetic light for body hair obtains a preferable cosmetic treatment enhancement effect and side effect inhibition effect as compared to when the intensity integral is larger in a wavelength range of 400 nm to 850 nm than in the wavelength range of 950 nm to 1100 nm.

The present invention is not limited to the embodiments, and may be modified as described below, for example.

The cosmetic light for body hair of the first embodiment has a maximum peak P1 within the 900 nm to 1000 nm range W20. However, the wavelength range in which the maximum peak P1 is formed is not limited to the details exemplified in the embodiment. A modification of the cosmetic light for body hair has the maximum peak P1 in the 850 nm to 900 nm range W12, the 1000 nm to 1100 nm range W30, or the 1100 nm to 1200 nm range W40, for example. Even when the wavelength range in which the maximum peak P1 is formed differs from the embodiments, the body hair optical cosmetic device 10 obtains advantages (1) to (4) of the first embodiment when the integral SX1 is smaller than the integral SX2.

The cosmetic light for body hair of the first embodiment has no peaks in the 400 nm to 850 nm wavelength range WX1. However, the number of peaks formed in the 400 nm to 850 nm wavelength range WX1 is not limited to the exemplified details in the embodiment. A modification of the cosmetic light for body hair has one or more peaks in the 400 nm to 850 nm wavelength range WX1, for example. It is preferable that a peak of the 400 nm to 850 nm wavelength range WX1 is smaller than the peak of 850 nm to 1200 nm range WX2. Even when the number of peaks in the 400 nm to 850 nm wavelength range WX1 differs from that in the embodiments, the optical cosmetic device for body hair obtains at least advantages (1) to (4) of the first embodiment when the integral SX1 is smaller than the integral SX2.

The cosmetic light for body hair of the second embodiment has a maximum peak P2 in the 800 nm to 850 nm range W11. However, the wavelength range in which the maximum peak P2 is formed is not limited to the details exemplified in the embodiments. A modification of the cosmetic light for body hair has a maximum peak P2 in the 850 nm to 900 nm range W12 or the 900 nm to 1000 nm range W20, for example. Even when the wavelength range in which the maximum peak P2 is formed differs from that of the embodiments, the body hair optical cosmetic device 10 obtains at least advantages (1) to (4) of the first embodiment when the integral SX1 is smaller than the integral SX2.

The cosmetic light for body hair of the third embodiment has a maximum peak P3 within the 850 nm to 900 nm range W12. However, the wavelength range in which the maximum peak P3 is formed is not limited to the details exemplified in the embodiments. A modification of the cosmetic light for body hair has the maximum peak P3 in the 900 nm to 1000 nm range W20, for example. Even when the wavelength range in which the maximum peak P3 is formed differs from the embodiments, the body hair optical cosmetic device 10 obtains at least advantages (1) to (4) of the first embodiment when the integral SX1 is smaller than the integral SX2.

The cosmetic light for body hair of the first embodiment to third embodiment contains a component of a wavelength range of less than 700 nm. However, the light source spectrum of the wavelength range of less than 700 nm is not limited to the details exemplified in each of the embodiments. A modification of the cosmetic light for body hair does not completely include a component of a wavelength range of less than 700 nm, for example.

The cosmetic light for body hair of the first embodiment to the third embodiment contains a component of a wavelength range of less than 800 nm. However, the light source spectrum of the wavelength range less than 800 nm is not limited to the details exemplified in each of the embodiments. A modification of the cosmetic light for body hair does not completely include a component in the wavelength range of less than 800 nm, for example.

In the first embodiment to the third embodiment, the 400 nm to 850 nm range WX1 may be a wavelength range of 400 nm or greater to less than 850 nm, a wavelength range longer than 400 nm to less than 850 nm, or a wavelength range of longer than 400 nm to 850 nm or less.

In the first embodiment to the third embodiment, the 850 nm to 1200 nm range WX2 may be a wavelength range of 850 nm or greater to less than 1200 nm, a wavelength range of longer than 850 nm to less than 1200 nm, a wavelength range longer than 850 nm to 1200 nm or less.

In the first embodiment to the third embodiment, the 800 nm to 900 nm range W10 may for example be a wavelength range of 800 nm or greater to less than 900 nm, a wavelength range of longer than 800 nm to less than 900 nm, or a wavelength range of longer than 800 nm to 900 nm or less.

In the first embodiment to the third embodiment, the 900 nm to 1000 nm range W20 may be, for example, a wavelength range of 900 nm or greater to less than 1000 nm, a wavelength range of longer than 900 nm to less than 1000 nm, or a wavelength range longer than 900 nm to 1000 nm or less.

In the first embodiment to the third embodiment, the 1000 nm to 1100 nm range W30 may be, for example, a wavelength range of 1000 nm or greater to less than 1100 nm, a wavelength range longer than 1000 nm to less than 1100 nm, or a wavelength range longer than 1000 nm to 1100 nm or less.

In the first embodiment to the third embodiment, the 1100 nm to 1200 nm range W40 may be a wavelength range of 1000 nm or greater to less than 1100 nm, a wavelength range of longer than 1000 nm to less than 1100 nm, or a wavelength range of longer than 1000 nm to 1100 nm or less.

The body hair optical cosmetic device 10 of the first embodiment to the third embodiment has a lens 36 formed of acrylics, polycarbonates, or glass. However, the configuration of the lens 36 is not limited to the details exemplified in the embodiments. A modification of the lens can have a configuration in which a light absorbing component is mixed in a substrate, for example.

The configurations of the lens 36 and the optical filter 37 of the body hair optical cosmetic device 10 of the first embodiment to the third embodiment are not limited to the details exemplified in the embodiments. A modification of the optical cosmetic device for body hair can have a lens integrated with a filter.

The body hair optical cosmetic device 10 in each of the first to third embodiments defines the intensity of the cosmetic light for body hair with spectral irradiance. However, the intensity of the cosmetic light for body hair is not limited to the details exemplified in the embodiments. For example, the intensity of the cosmetic light for body hair may be defined by a spectroradiometric energy density ($\mu J/cm^2/nm$).

An optical system of the optical cosmetic device 10 for body hair includes the light source 34, a wavelength selecting element such as the optical filter 37, and the lens 36. However, as long as the desired cosmetic light for body hair can be emitted, one or both of the optical filter 37 and lens 36 may be omitted.

Some of the above embodiments and modifications may be combined freely as long as there are technical contradictions.

EXAMPLES

Through experiments, the inventors of the present application have studied the influence of cosmetic light for body hair in each of the first to third embodiments and a comparative example on body hair.

Figure 5:
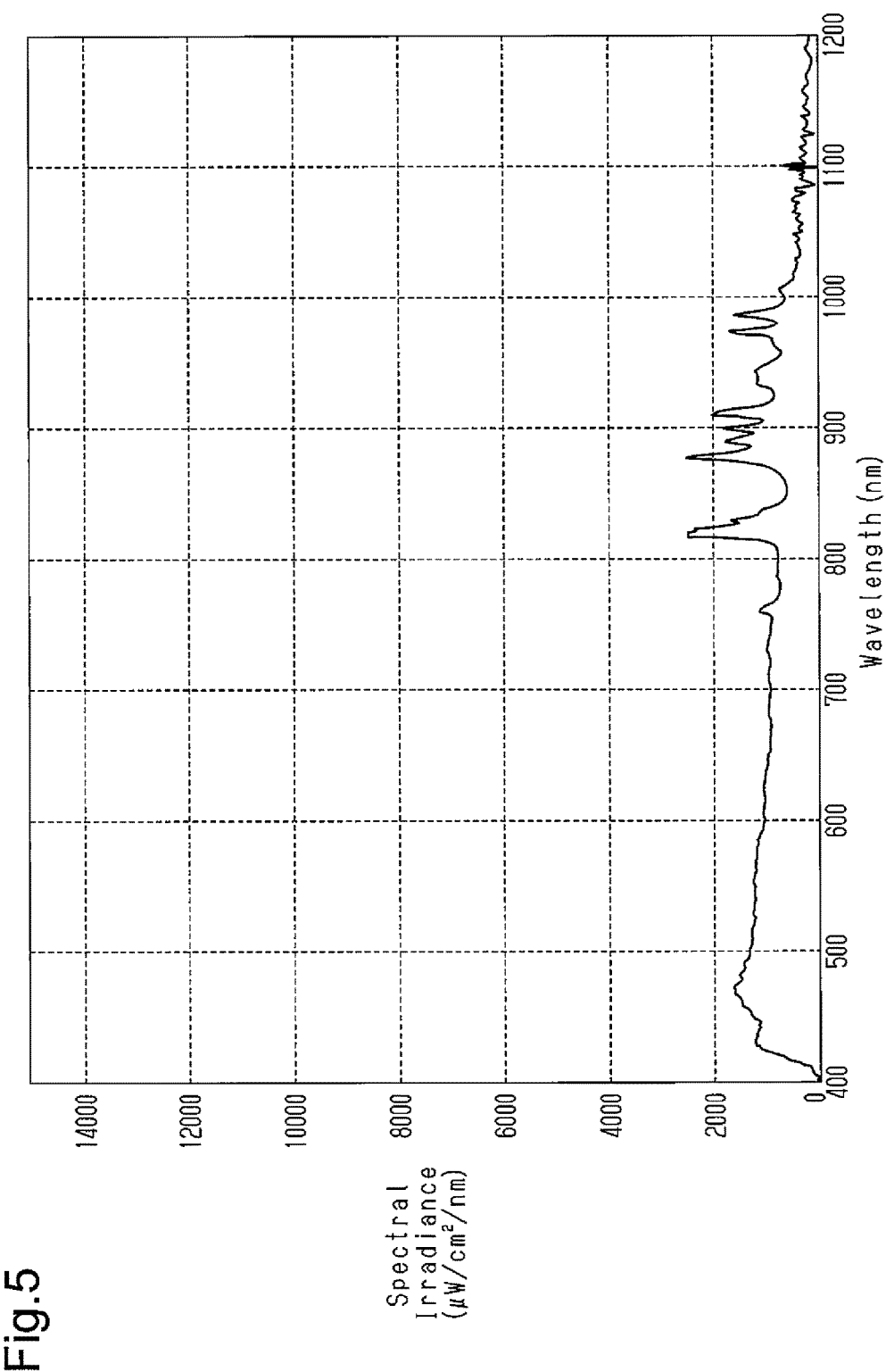
FIG. 5 is a graph showing a light source spectrum of cosmetic light for body hair in a comparative example.

In the comparative example, a device differing from the optical cosmetic device 10 only in the type of the lens 36 and optical filter 37 was used. As shown in FIG. 5, the light of the device of the comparative example is a spectrum of a standard xenon flash lamp.

Body hair was shaved from a predetermined portion in each back of five experimental mice, which were irradiated with light, to form a square observation area. Each side of the square observation area was 2 cm. In the same manner as the mice irradiated with light, observation areas were formed in five control mice, which were not irradiated with light.

In each of the experiments conducted under different conditions, the experimental mice, or light irradiated mice, were irradiated with light, whereas the control mice, or non-light irradiated mice, were not irradiated with light. For each experimental mouse, the growth of body hair and changes in the skin in the observation area were observed after the light irradiation. For each control mouse, the growth of body hair and changes in the skin in the observation area were also observed as the same timing.

The number of body hairs and the length of the hairs in the observation area were measured through an image analysis of the observation area. The measured number of body hairs was multiplied by the total length of the hairs to obtain the body hair amount.

The average body hair amount for the light irradiated mice was divided by the average body hair amount for the non-light irradiated mice to yield the ratio of hair growth inhibition.

The hair growth inhibition ratio of 1 indicates that the growth of body hair of the light irradiated mice is the same as the growth of body hair of the non-light irradiated mice. The hair growth inhibition ratio closer to 0 indicates that the growth of body hair of the light irradiated mice is slower than the growth of body hair of the non-light irradiated mice, thus indicating that the light has a higher effect of inhibiting the growth of hair.

The experimental conditions were set in the manner described below. The conditions include the light energy density, the irradiation time, the irradiation cycle, the unit number of times of irradiation, the total number of times of irradiation, the observation start period, and the progress observation period.

The light energy density was set to three values, namely, 0.2 ($J/cm^2$), 1.0 ($J/cm^2$), and 1.5 ($J/cm^2$). The light energy density can be changed by supplying a different amount of power to the light source 34.

The irradiation time was set to three values, namely, 0.6 ms, 1.0 ms, and 2.0 ms. The irradiation time can be adjusted by a signal provided from the control unit 50 to the light source 34.

The irradiation cycle was set to two values, namely, 30 seconds and 60 seconds. The irradiation cycle can be adjusted by a signal providing from the control unit 50 to the light source 34.

The unit number of times of irradiation was set to two values, namely, 4 times per day and 8 times per day. The experiments were conducted for four days. The total number of times of irradiation was thus 16 times and 32 times.

In the observation start period immediately after the formation of the observation areas in the light irradiated mice and the non-light irradiated mice, these mice underwent the first irradiation in their observation areas.

The images of the observation areas were captured at the end of the final irradiation (referred to as immediately after the irradiation), one week after the irradiation and two weeks after the irradiation. The period during which the images were captured may be referred to as the observation period.

Table 1 shows the results with the irradiation cycle of 30 seconds, the number of irradiation times of 4 times/day, and the total number of irradiation times of 16 times.

Table 2 shows the results with the irradiation cycle of 30 seconds, the number of irradiation times of 8 times/day, and the total number of irradiation times of 32 times.

Table 3 shows the results under the irradiation cycle of 60 seconds, the number of irradiation times of 4 times/day, and the total number of irradiation times of 16 times.

Table 4 shows the results under the irradiation cycle of 60 seconds, the number of irradiation times of 8 times/day, and the total number of irradiation times of 32 times.

TABLE 1

| Energy density of light ($J/cm^2$) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| 0.2 | 0.6 | Immediately after irradiation | 0.8 | 0.7 | 0.7 | 0.8 |
| | | 1 week later | 0.6 | 0.6 | 0.6 | 0.7 |
| | | 2 weeks later | 0.5 | 0.4 | 0.4 | 0.8 |
| | 1 | Immediately after irradiation | 0.8 | 0.7 | 0.7 | 0.8 |
| | | 1 week later | 0.7 | 0.6 | 0.5 | 0.7 |
| | | 2 weeks later | 0.5 | 0.4 | 0.4 | 0.7 |

TABLE 1-continued

| Energy density of light (J/cm 2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| | 2 | Immediately after irradiation | 0.8 | 0.7 | 0.7 | 0.8 |
| | | 1 week later | 0.6 | 0.5 | 0.4 | 0.7 |
| | | 2 weeks later | 0.5 | 0.4 | 0.4 | 0.7 |
| 1 | 0.6 | Immediately after irradiation | 0.7 | 0.7 | 0.7 | 0.8 |
| | | 1 week later | 0.6 | 0.5 | 0.5 | 0.7 |
| | | 2 weeks later | 0.4 | 0.4 | 0.4 | 0.8 |
| | 1 | Immediately after irradiation | 0.7 | 0.7 | 0.7 | 0.8 |
| | | 1 week later | 0.6 | 0.6 | 0.4 | 0.7 |
| | | 2 weeks later | 0.4 | 0.4 | 0.4 | 0.8 |
| | 2 | Immediately after irradiation | 0.7 | 0.7 | 0.7 | 0.8 |
| | | 1 week later | 0.7 | 0.5 | 0.4 | 0.7 |
| | | 2 weeks later | 0.4 | 0.5 | 0.4 | 0.8 |
| 1.5 | 0.6 | Immediately after irradiation | 0.6 | 0.6 | 0.6 | 0.7 |
| | | 1 week later | 0.4 | 0.6 | 0.5 | 0.6 |
| | | 2 weeks later | 0.4 | 0.4 | 0.4 | 0.7 |
| | 1 | Immediately after irradiation | 0.6 | 0.7 | 0.6 | 0.7 |
| | | 1 week later | 0.6 | 0.5 | 0.4 | 0.7 |
| | | 2 weeks later | 0.4 | 0.4 | 0.4 | 0.8 |
| | 2 | Immediately after irradiation | 0.6 | 0.6 | 0.6 | 0.7 |
| | | 1 week later | 0.6 | 0.5 | 0.4 | 0.6 |
| | | 2 weeks later | 0.5 | 0.4 | 0.4 | 0.8 |

*Irradiation cycle = 30 secs, No. of times of unit irradiation = 4 times/day, Total no. of irradiation = 16 times

TABLE 2

| Energy density of light (J/cm 2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| 0.2 | 0.6 | Immediately after irradiation | 0.8 | 0.7 | 0.7 | 0.8 |
| | | 1 week later | 0.6 | 0.5 | 0.5 | 0.7 |
| | | 2 weeks later | 0.5 | 0.4 | 0.4 | 0.8 |
| | 1 | Immediately after irradiation | 0.8 | 0.7 | 0.7 | 0.8 |
| | | 1 week later | 0.7 | 0.6 | 0.5 | 0.8 |
| | | 2 weeks later | 0.5 | 0.4 | 0.4 | 0.8 |
| | 2 | Immediately after irradiation | 0.8 | 0.7 | 0.7 | 0.8 |
| | | 1 week later | 0.5 | 0.5 | 0.4 | 0.7 |
| | | 2 weeks later | 0.5 | 0.4 | 0.4 | 0.7 |
| 1 | 0.6 | Immediately after irradiation | 0.8 | 0.7 | 0.7 | 0.8 |
| | | 1 week later | 0.6 | 0.5 | 0.5 | 0.7 |
| | | 2 weeks later | 0.4 | 0.4 | 0.4 | 0.8 |
| | 1 | Immediately after irradiation | 0.7 | 0.7 | 0.7 | 0.8 |
| | | 1 week later | 0.5 | 0.6 | 0.4 | 0.8 |
| | | 2 weeks later | 0.4 | 0.4 | 0.4 | 0.8 |
| | 2 | Immediately after irradiation | 0.7 | 0.7 | 0.7 | 0.8 |
| | | 1 week later | 0.6 | 0.5 | 0.4 | 0.7 |
| | | 2 weeks later | 0.4 | 0.5 | 0.4 | 0.8 |
| 1.5 | 0.6 | Immediately after irradiation | 0.6 | 0.6 | 0.6 | 0.7 |
| | | 1 week later | 0.4 | 0.6 | 0.5 | 0.6 |
| | | 2 weeks later | 0.4 | 0.4 | 0.5 | 0.7 |
| | 1 | Immediately after irradiation | 0.8 | 0.7 | 0.6 | 0.7 |
| | | 1 week later | 0.8 | 0.5 | 0.4 | 0.8 |
| | | 2 weeks later | 0.4 | 0.4 | 0.4 | 0.8 |

TABLE 2-continued

| Energy density of light (J/cm^2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| | 2 | Immediately after irradiation | 0.8 | 0.6 | 0.6 | 0.7 |
| | | 1 week later | 0.8 | 0.5 | 0.4 | 0.6 |
| | | 2 weeks later | 0.5 | 0.4 | 0.4 | 0.6 |

* Irradiation cycle = 30 secs, No. of times of unit irradiation = 8 times/day, Total no. of irradiation = 32 times

TABLE 3

| Energy density of light (J/cm^2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| 0.2 | 0.6 | Immediately after irradiation | 0.8 | 0.7 | 0.7 | 0.8 |
| | | 1 week later | 0.6 | 0.6 | 0.5 | 0.7 |
| | | 2 weeks later | 0.5 | 0.4 | 0.4 | 0.8 |
| | 1 | Immediately after irradiation | 0.8 | 0.7 | 0.7 | 0.8 |
| | | 1 week later | 0.7 | 0.6 | 0.5 | 0.8 |
| | | 2 weeks later | 0.5 | 0.4 | 0.4 | 0.7 |
| | 2 | Immediately after irradiation | 0.8 | 0.7 | 0.7 | 0.8 |
| | | 1 week later | 0.6 | 0.4 | 0.4 | 0.7 |
| | | 2 weeks later | 0.5 | 0.4 | 0.4 | 0.7 |
| 1 | 0.6 | Immediately after irradiation | 0.7 | 0.7 | 0.7 | 0.8 |
| | | 1 week later | 0.6 | 0.5 | 0.5 | 0.7 |
| | | 2 weeks later | 0.4 | 0.4 | 0.4 | 0.7 |
| | 1 | Immediately after irradiation | 0.7 | 0.7 | 0.7 | 0.8 |
| | | 1 week later | 0.5 | 0.6 | 0.4 | 0.7 |
| | | 2 weeks later | 0.4 | 0.4 | 0.4 | 0.8 |
| | 2 | Immediately after irradiation | 0.7 | 0.7 | 0.7 | 0.8 |
| | | 1 week later | 0.7 | 0.5 | 0.4 | 0.8 |
| | | 2 weeks later | 0.4 | 0.5 | 0.4 | 0.8 |
| 1.5 | 0.6 | Immediately after irradiation | 0.6 | 0.6 | 0.6 | 0.7 |
| | | 1 week later | 0.4 | 0.5 | 0.5 | 0.6 |
| | | 2 weeks later | 0.4 | 0.4 | 0.4 | 0.7 |
| | 1 | Immediately after irradiation | 0.6 | 0.7 | 0.6 | 0.7 |
| | | 1 week later | 0.6 | 0.4 | 0.4 | 0.7 |
| | | 2 weeks later | 0.4 | 0.4 | 0.4 | 0.8 |
| | 2 | Immediately after irradiation | 0.6 | 0.6 | 0.6 | 0.7 |
| | | 1 week later | 0.6 | 0.5 | 0.4 | 0.6 |
| | | 2 weeks later | 0.5 | 0.4 | 0.4 | 0.6 |

* Irradiation cycle = 60 secs, No. of times of unit irradiation = 4 times/day, Total no. of times of irradiation = 16 times

TABLE 4

| Energy density of light (J/cm^2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| 0.2 | 0.6 | Immediately after irradiation | 0.8 | 0.7 | 0.7 | 0.8 |
| | | 1 week later | 0.7 | 0.6 | 0.5 | 0.7 |
| | | 2 weeks later | 0.5 | 0.4 | 0.4 | 0.8 |

TABLE 4-continued

| Energy density of light (J/cm 2) | Irradiation time (ms) | Follow-up observation period | Hair inhibition rate (light-irradiated body hair amount/non-irradiated body hair amount) | | | |
|---|---|---|---|---|---|---|
| | | | 1st Embodiment | 2nd Embodiment | 3rd Embodiment | Comparative Example |
| 1 | 1 | Immediately after irradiation | 0.8 | 0.8 | 0.7 | 0.8 |
| | | 1 week later | 0.7 | 0.6 | 0.5 | 0.7 |
| | | 2 weeks later | 0.5 | 0.4 | 0.4 | 0.7 |
| | 2 | Immediately after irradiation | 0.8 | 0.7 | 0.7 | 0.8 |
| | | 1 week later | 0.6 | 0.5 | 0.4 | 0.7 |
| | | 2 weeks later | 0.5 | 0.4 | 0.4 | 0.8 |
| | 0.6 | Immediately after irradiation | 0.7 | 0.8 | 0.7 | 0.8 |
| | | 1 week later | 0.6 | 0.5 | 0.5 | 0.7 |
| | | 2 weeks later | 0.4 | 0.4 | 0.4 | 0.8 |
| | 1 | Immediately after irradiation | 0.7 | 0.7 | 0.8 | 0.8 |
| | | 1 week later | 0.6 | 0.6 | 0.4 | 0.7 |
| | | 2 weeks later | 0.4 | 0.4 | 0.4 | 0.8 |
| | 2 | Immediately after irradiation | 0.7 | 0.7 | 0.7 | 0.8 |
| | | 1 week later | 0.7 | 0.5 | 0.4 | 0.7 |
| | | 2 weeks later | 0.4 | 0.5 | 0.4 | 0.8 |
| 1.5 | 0.6 | Immediately after irradiation | 0.6 | 0.6 | 0.6 | 0.7 |
| | | 1 week later | 0.4 | 0.6 | 0.5 | 0.6 |
| | | 2 weeks later | 0.4 | 0.4 | 0.4 | 0.7 |
| | 1 | Immediately after irradiation | 0.6 | 0.7 | 0.6 | 0.7 |
| | | 1 week later | 0.6 | 0.5 | 0.4 | 0.7 |
| | | 2 weeks later | 0.4 | 0.4 | 0.4 | 0.6 |
| | 2 | Immediately after irradiation | 0.6 | 0.6 | 0.6 | 0.7 |
| | | 1 week later | 0.6 | 0.5 | 0.4 | 0.6 |
| | | 2 weeks later | 0.5 | 0.4 | 0.4 | 0.6 |

* Irradiation cycle = 60 secs, No. of times of unit irradiation = 8 times/day, Total no. of times of irradiation = 32 times The tables show that the hair inhibition rates of the first embodiment to the third embodiment and the comparative example decreases as the energy density of light increases. The hair inhibition rates of the first embodiment to the third embodiment are generally smaller than the hair inhibition rate of the comparative example from immediately after irradiation. The hair inhibition rates of the first embodiment to the third embodiment approaches 0 as time elapses from immediately after the light irradiation, and the difference of the hair inhibition rate of each embodiment increases from that of the comparative example. More specifically, the cosmetic light for body hair of the first to third embodiments have a body hair cosmetic treatment effect for a longer period than the light of the comparative example.

The skin in the observation areas of the light irradiated mice and the non-light irradiated mice was observed to quantitatively evaluate the influence of the cosmetic light for body hair of the first to third embodiments and the comparative example on the skin.

A granular layer was collected from the skin of the observation area of each mouse immediately after the irradiation. The granular layers were compared. There was substantially no difference between the granular layers from the light irradiated mice irradiated with the cosmetic light for body hair of the embodiments and the granular layers from the non-light irradiated mice. There was a substantial difference between the granular layers from the light irradiated mice irradiated with the light of the comparative example and the granular layers from the non-light irradiated mice. This finding indicates that the influence of the light of the comparative example is greater than the influence of the cosmetic light for body hair of the embodiments.

[Clause 1] The optical cosmetic device for body hair according to any one of claims 1 to 7, wherein the intensity integral of the cosmetic light for body hair is larger in a wavelength range of 1000 nm to 1100 nm than in a wavelength range of 1100 nm to 1200 nm. Such an optical cosmetic device for body hair improves the body hair cosmetic treatment effect compared to when the intensity integral is smaller in the wavelength range of 1000 nm to 1100 nm than in the wavelength range of 1100 nm to 1200 nm.

[Clause 2] The optical cosmetic device for body hair according to any one of claims 1 to 7 and clause 1, wherein the intensity integral of the cosmetic light for body hair is larger in a wavelength range of 900 nm to 1000 nm than in a wavelength range of 1100 nm to 1200 nm. Such an optical cosmetic device for body hair configured improves the body hair cosmetic treatment effect as compared to when the intensity integral is smaller in the wavelength range of 900 nm to 1000 nm than in the wavelength range of 1100 nm to 1200 nm.

[Clause 3] The optical cosmetic device for body hair according to any one of claims 1 to 7 and clauses 1 and 2, wherein the intensity integral of the cosmetic light for body hair is larger in a wavelength range of 850 nm to 900 nm than in a wavelength range of 1100 nm to 1200 nm. Such an optical cosmetic device for body hair improves the body hair cosmetic treatment effect as compared to when the intensity integral is smaller in the wavelength range of 850 nm to 900 nm than in the wavelength range of 1100 nm to 1200 nm.

The invention claimed is:

1. An optical cosmetic device for body hair, comprising:
an optical system that emits cosmetic light for body hair, wherein an intensity integral of the cosmetic light for body hair is larger in a wavelength range of 800 nm to 1200 nm than in a wavelength range of 400 nm to 800 nm, an intensity integral of the cosmetic light for body hair is smaller in a wavelength range of 400 nm to 850 nm than in a wavelength range of 850 nm to 900 nm, and the cosmetic light for body hair has no intensity peaks in a wavelength range of 800 nm to 860 nm, in order to inhibit reproduction and growth of body hair on a skin where the cosmetic light for body hair is irradiated,
wherein the intensity integral of the cosmetic light for body hair is smaller in the wavelength range of 400 nm to 850 nm than in the wavelength range of 950 nm to 1200 nm.

2. The optical cosmetic device for body hair according to claim 1, wherein the intensity integral of the cosmetic light for body hair is larger in the wavelength range of 800 nm to 1000 nm than in the wavelength range of 1000 nm to 1200 nm.

3. The optical cosmetic device for body hair according to claim 2, wherein the intensity integral of the cosmetic light for body hair is larger in the wavelength range of 850 nm to 1000 nm than in the wavelength range of 1000 nm to 1200 nm.

4. The optical cosmetic device for body hair according to claim 3, wherein the intensity integral of the cosmetic light for body hair is larger in the wavelength range of 900 nm to 1000 nm than in the wavelength range of 1000 nm to 1200 nm.

5. The optical cosmetic device for body hair according to claim 1, wherein
the optical system comprises a xenon lamp and a band-pass filter,
the xenon lamp emits light in a wavelength range of 400 nm to 1200 nm, and
the band-pass filter forms the cosmetic light for body hair by cutting light of wavelengths other than the wavelength range of 800 nm to 1200 nm.

6. The optical cosmetic device for body hair according to claim 1, wherein the cosmetic light for body hair has a plurality of peaks in a wavelength range of greater than 860 nm to equal to or less than 1200 nm.

* * * * *